United States Patent [19]

Espitalie et al.

[11] 4,229,181
[45] Oct. 21, 1980

[54] METHOD FOR DETERMINING OIL-RELATED CHARACTERISTICS OF GEOLOGICAL SEDIMENTS FROM SMALL SAMPLES THEREOF

[75] Inventors: Jean Espitalié, le Vésinet; Jean-Loup Laporte, Rueil Malmaison; Marcel Madec, Suresnes; François Marquis, Saint Prix, all of France

[73] Assignee: Institut Frahcais du Petrole, France

[21] Appl. No.: 940,753

[22] Filed: Sep. 8, 1978

Related U.S. Application Data

[63] Continuation-in-part of Ser. No. 760,524, Jan. 19, 1977, Pat. No. 4,153,415.

[30] Foreign Application Priority Data

Jan. 20, 1976 [FR] France .............................. 76 01765
Nov. 12, 1976 [FR] France .............................. 76 34402

[51] Int. Cl.² ........................................................ G01N 31/12
[52] U.S. Cl. ............................ 23/230 EP; 23/230 PC; 422/80
[58] Field of Search .................... 23/230 PC, 230 EP; 422/78, 80

[56] References Cited

U.S. PATENT DOCUMENTS

| 2,686,211 | 8/1954 | Cargill | 422/78 X |
| 3,033,287 | 5/1962 | Bond | 23/230 EP |
| 3,574,549 | 4/1971 | Eggertsen | 23/230 PC |
| 3,661,527 | 5/1972 | Eggertsen et al. | 23/230 PC |
| 3,703,355 | 11/1972 | Takahasi et al. | 23/230 PC |
| 3,834,122 | 9/1974 | Allison et al. | 23/230 EP X |
| 3,861,874 | 1/1975 | Krc | 23/230 PC |
| 3,953,171 | 4/1976 | Espitalie et al. | 23/230 EP |
| 4,135,881 | 1/1979 | Bakx et al. | 230/230 PC |
| 4,153,415 | 5/1979 | Espitalie et al. | 23/230 EP |

*Primary Examiner*—Arnold Turk
*Attorney, Agent, or Firm*—Craig & Antonelli

[57] ABSTRACT

Sample of geological sediment is heated preferably to a first temperature in the range from 50° C. to 65° C., then to a second temperature in the range from 200° C. to 350° C. and finally to a third temperature in the range from 550° C. to 600° C. Oil-related characteristics of the sediments are derived from the respective amounts of hydrocarbons released by the sample during these three steps.

12 Claims, 7 Drawing Figures

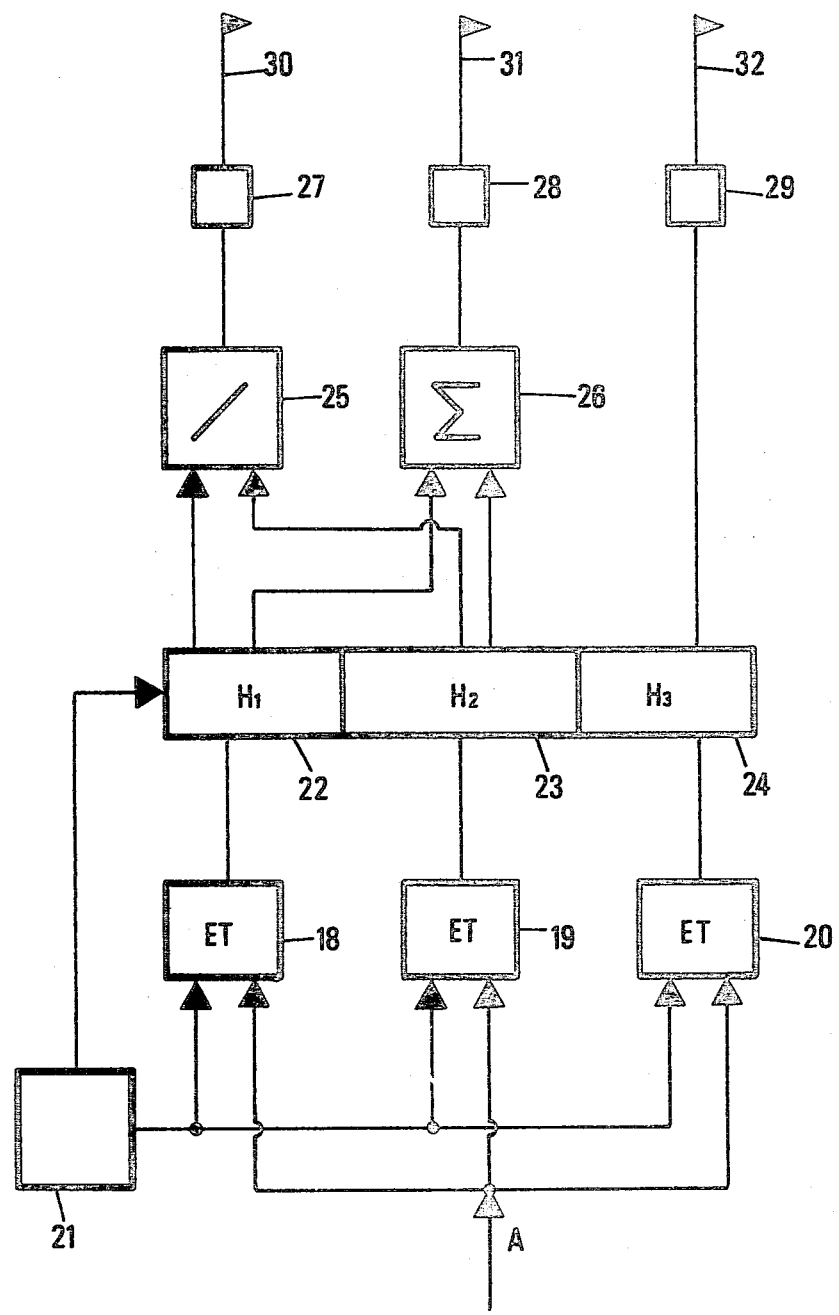

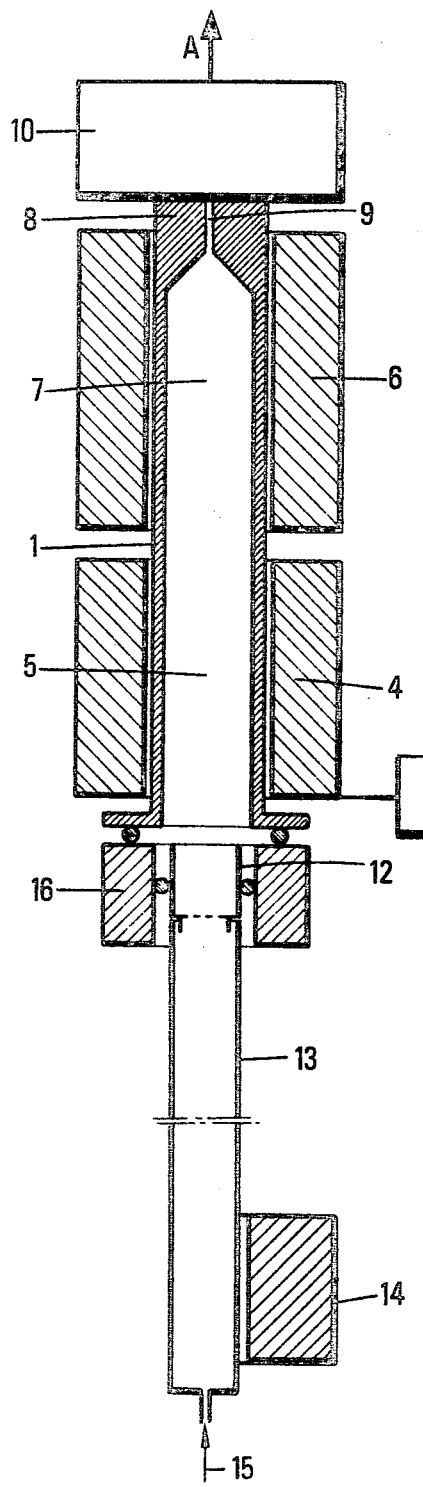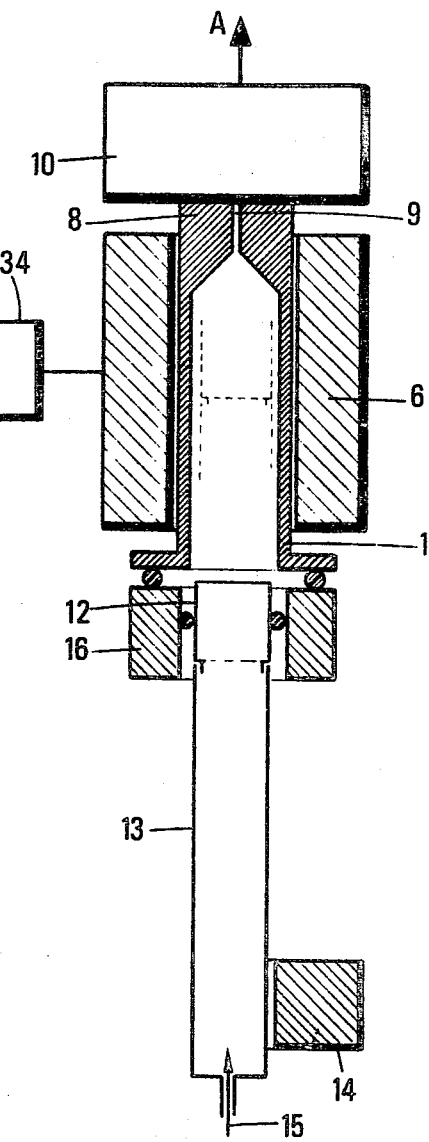

METHOD FOR DETERMINING OIL-RELATED CHARACTERISTICS OF GEOLOGICAL SEDIMENTS FROM SMALL SAMPLES THEREOF

This is a continuation-in-part of patent application Ser. No. 760,524, filed 01/19/1977, issued as U.S. Pat. No. 4,153,415, relating to the determination of at least some of the oil-related characteristics of a geological sediment.

These characteristics are derived from a first and a second parameters which are obtained successively by first heating a sample of the geological sediment to a temperature capable of releasing substantially the whole amount of the hydrocarbons initially contained in the sample, this first temperature being however insufficient for pyrolyzing the insoluble organic material contained in the sample, said first parameter being representative of the amount of hydrocarbons initially present in the sample, then raising the sample temperature to a second value so as to pyrolyze substantially the whole amount of the organic material present in the sample, said second parameter being representative of the amount of hydrocarbon products resulting from the pyrolysis of the organic material.

It is thus possible to determine for example, but not exclusively, the capacity of the geological sediment to produce hydrocarbons either right now or in the future, or to be a good source-rock (or mother-rock), or a hydrocarbon-containing reservoir rock.

The present invention provides a method of the above-described type for determining in particular in a simple manner whether the hydrocarbons initially contained in the sample are in the gaseous or liquid state.

Moreover the invention provides an apparatus for obtaining the desired data, and a preferred embodiment of this apparatus is so designed as to be suitable for tests performed on the field.

The invention will be understood and all the advantages thereof become apparent from the following description of non-limitative embodiments illustrated by the accompanying drawings, wherein:

FIGS. 5 to 7 represent three further embodiments of the invention.

According to the invention the sample of sediments to be examined is positioned in a flow of carrier gas and its temperature is brought to a first value sufficient to extract from the sample only the gaseous hydrocarbons initially contained therein; the amount of these gaseous hydrocarbons is measured; then the temperature of the sample is raised to a second value at which all the liquid hydrocarbons initially contained in the sample are vaporized and the amount of these liquid hydrocarbons is measured, said two temperature values being however insufficient for pyrolyzing the insoluble organic material contained in the sample. The temperature of the sample is then increased to a third value sufficient to pyrolyze the whole amount of the insoluble organic material obtained in the sample and the amount of the hydrocarbon products resulting from this pyrolysis is measured. From the three above-indicated measurements there is derived at least one characteristic of the geological formation wherefrom the sample has been collected.

The first temperature value is usually lower than 90° C. and preferably in the range from 50° C. to 65° C., the second value is lower than 350° C. and usually in the range from 200° C. to 350° C., and the third temperature value is comprised between 400° C. and 700° C., and preferably in the range from 550° C. to 600° C.

Figure 1:
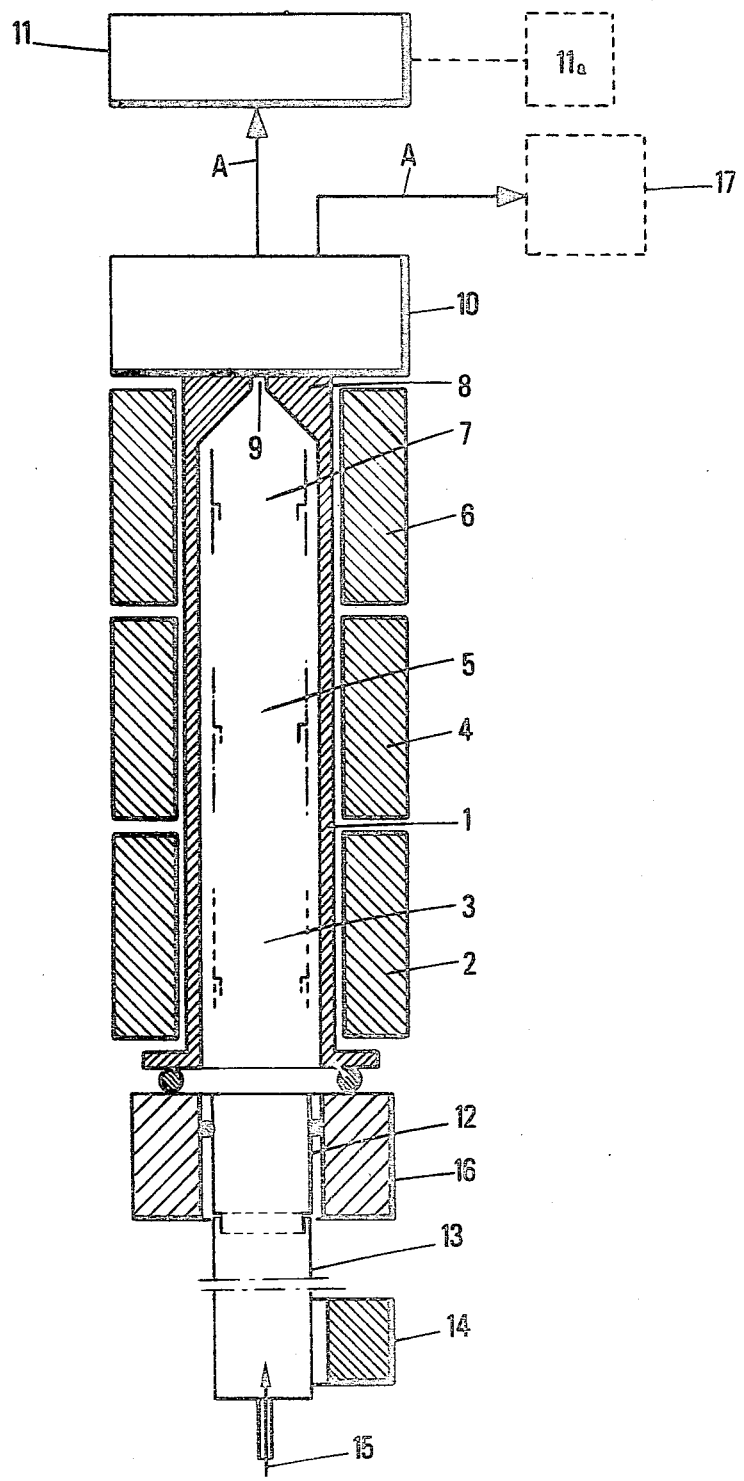
FIG. 1 shows a first embodiment of the invention.

A first embodiment of apparatus for carrying out the method according to the invention is diagrammatically illustrated in FIG. 1.

This apparatus comprises a tube or housing 1 which can be heated. This tube is preferably substantially vertical. In the embodiment illustrated by FIG. 1, the apparatus comprises means 2 for heating the lower part 3 of tube 1, means 4 for heating the intermediate part 5 of tube 1 and means 6 for heating the upper part 7 of tube 1. These heating means may be of conventional type and will surround tube 1. Alternatively, the tube can be made of three electrically conducting parts separated by insulating portions, heating being then achieved by supplying electric current to the conducting parts of tube 1.

Each heating means may comprise a temperature regulating and/or programming means which may be of any conventional type and has not been shown.

The heating means 2 is adapted to maintain part 3 of tube 1 at a temperature lower than 90° C. and preferably in the range from 50° C. to 65° C.

The heating means 4 is adapted to maintain part 5 of tube 1 at a temperature comprised between 90° C. and 350° C., more particularly in the range from 200° to 350°.

The heating means 6 is adapted to maintain the upper part 7 of tube 1 at a temperature higher than 400° C., and lower than 700° C., preferably between 550° C. and 600° C.

The upper part 8 of tube 1 is maintained at the same temperature as portion 7 of tube 1, which communicates through a duct 9 of small diameter with a device 10 for detecting and measuring the amount of hydrocarbon compounds discharged from tube 1.

The device for selectively detecting the hydrocarbon compounds will, for example, comprise a flame ionization detector, of conventional use in gas chromatography.

The detector 10 delivers a signal A representative of the measured amounts of hydrocarbon compounds. This signal may be transmitted to a recording device 11, so as to be displayed, if desired, and/or to data processing means illustrated in mixed line in FIG. 1.

The apparatus according to the invention also comprises a cup 12 wherein is placed the sample to be analyzed. This cup may be displaced, so as to be introduced into tube 1, by any suitable means, such as, for example, a piston 13 associated with automatic or manual displacement means 14, which may be constituted by a cylinder forming with piston 13 a double-acting jack connected to a source of fluid, or, alternately, by a toothed wheel (or pinion) which can be rotated and co-operates with a rack integral with piston 13.

Piston 13 will preferably be hollow. It is connected at its lower part to a pipe 15 delivering a carrier gas which may be a non-oxidizing gas, such as hydrogen, or an inert gas (nitrogen, helium . . . )

Means 16 provides for insulation and sealing around piston 13. Such means may optionally be displaceable to facilitate the introduction of the sample into cup 12.

The sample to be analyzed is introduced into cup 12. This sample, preferably of small size, with a weight not exceeding 200 mg, can be analyzed without preliminary treatment, even if it originates from drill cuttings. Alternatively the sample may be subjected to some preliminary treatments such as grinding, etc ... The device is then in its position illustrated in solid line in FIG. 1. The heating means 2, 4 and 6 are energized and when each of parts 3, 5 and 7 has reached the desired temperature the cup 12 is introduced at time $t_0$ into tube 1, first in the lower part 3 thereof (position shown in dashed line) and the device is fed with carrier gas which permanently scavenges the sample.

Under the action of the temperature, which is set at a value in the range from 50° C. to 65° C., the whole amount of the gaseous hydrocarbons initially contained in the sample is released from the sample, then, carried away with the carrier gas and then detected, this amount being measured by device 10.

At time $t_1$, when substantially all the gaseous hydrocarbons have been extracted from the sample, cup 12 is displaced by piston 13 so as to be positioned in the middle part 5 of tube 1 position shown in mixed line in FIG. 1. Under the influence of the temperature (in the range from 200° C. to 350° C.) the whole amount of the liquid hydrocarbons initially contained in the sample is vaporized, then detected and measured by detector 10.

At time $t_2$, when substantially all the liquid hydrocarbons have been vaporized, piston 13 is rapidly moved upwardly (FIG. 1) and cup 12 is positioned in part 7 of tube 1 (position illustrated in thin line). The rate of this displacement is such that the sample is subjected to a temperature variation of at least 20° C. by minute. Under the influence of the high temperature (preferably in the range from 550° C. to 600° C.) the whole insoluble organic material contained in the sample is pyrolyzed. When, at time $t_3$, the whole amount of the hydrocarbon products resulting from this pyrolysis has been detected and measured by device 11, piston 13 may be drawn back to its initial position (FIG.1).

Figure 2:
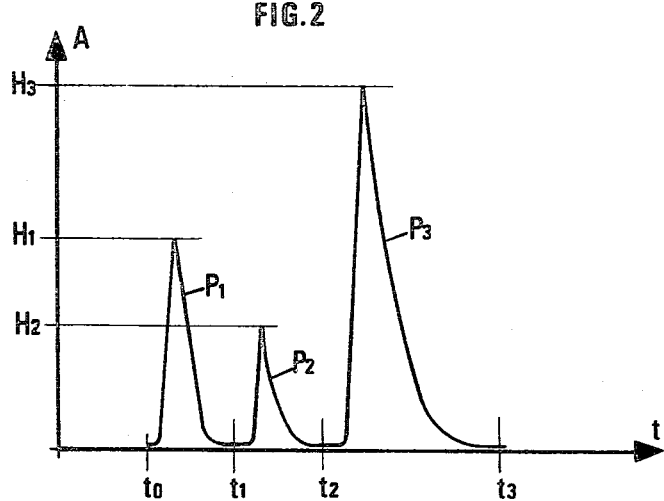
FIG. 2 shows the general shape of the signal A delivered by the detector.

FIG. 2 shows versus time the general shape of signal "A" delivered by device 10 between the instants $t_0$ and $t_3$. As it is apparent from this drawing, this signal generally comprises three separate peaks $P_1$, $P_2$ and $P_3$. The first peak, of amplitude $H_1$, appears during the time interval $[t_0-t_1]$ and corresponds to the gaseous hydrocarbons initially present in the sample. The second peak, of amplitude $H_2$, appears during the time interval $[t_1-t_2]$ and corresponds to the liquid hydrocarbons initially contained in the sample. The third peak, of amplitude $H_3$, appears during the time interval $[t_2-t_3]$ and corresponds to the hydrocarbon products resulting from pyrolysis of the insoluble organic material of the sample. When piston 13 is displaced through automatic means 14, such means may be actuated by signal A. For example, when, at time $t_1$, this signal has reached, while decreasing, a first lower limit, the means 14 moves piston 13 upwardly (FIG. 1) so as to bring cup 12 into portion 5 of tube 1. Similarly, when at time $t_2$, this signal has reached, while decreasing a second lower limit, the means 14 moves piston 13 upwardly so as to bring cup 12 into portion 7 of tube 1. When, at time $t_3$, the signal A has reached, while decreasing a third lower limit, the means moves piston 13 downwardly (FIG. 1), so as to bring cup 12 back to its initial position where it can be cooled and a new measuring cycle can begin.

Knowing the values $H_1$, $H_2$, and $H_3$ of peaks $P_1$, $P_2$ and $P_3$, it is possible to characterize the rock as follows:

(1) High values of $H_3$ depict a source rock of good quality containing the more hydrocarbons as, simultaneously, the values of the sum $(H_1+H_2)$ are high. This source rock will have produced more gaseous hydrocarbons than liquid hydrocarbons (gas-containing zone) if the ratio $H_1/H_2$ is greater than 1, this ratio being related to the degree of evolution of the insoluble organic material of the sediment. Conversely the source rock will have produced more liquid hydrocarbons than gaseous hydrocarbons when the value of the ratio $H_1/H_2$ is lower than 1 (oil-containing zone), (2) moderate or average values of $H_2$ depict a source-rock of average quality containing the more hydrocarbons as, simultaneously, the values of the sum $(H_1+H_2)$ are high, (3) low values of $H_3$ depict
  (a) a rock of no interest for hydrocarbon extraction when simultaneously the values of the sum $(H_1+H_2)$ are low
  (b) some indications on the presence of hydrocarbons when simultaneously the values of the sum $(H_1+H_2)$ are moderate and,
  (c) a source rock filled with hydrocarbons, when simultaneously the values of the sum $(H_1+H_2)$ are high, this source rock containing more gaseous hydrocarbons than liquid hydrocarbons when the ratio $H_1/H_2$ is greater than 1, and containing more liquid hydrocarbons than gaeseous hydrocarbons when the ratio $H_1/H_2$ is lower than 1.

It will be obviously also possible, without departing from the scope of the present invention, to consider the integrated values of signals $P_1$, $P_2$ and $P_3$, instead of their maximum or peak values $H_1$, $H_2$ and $H_3$.

Figure 3:
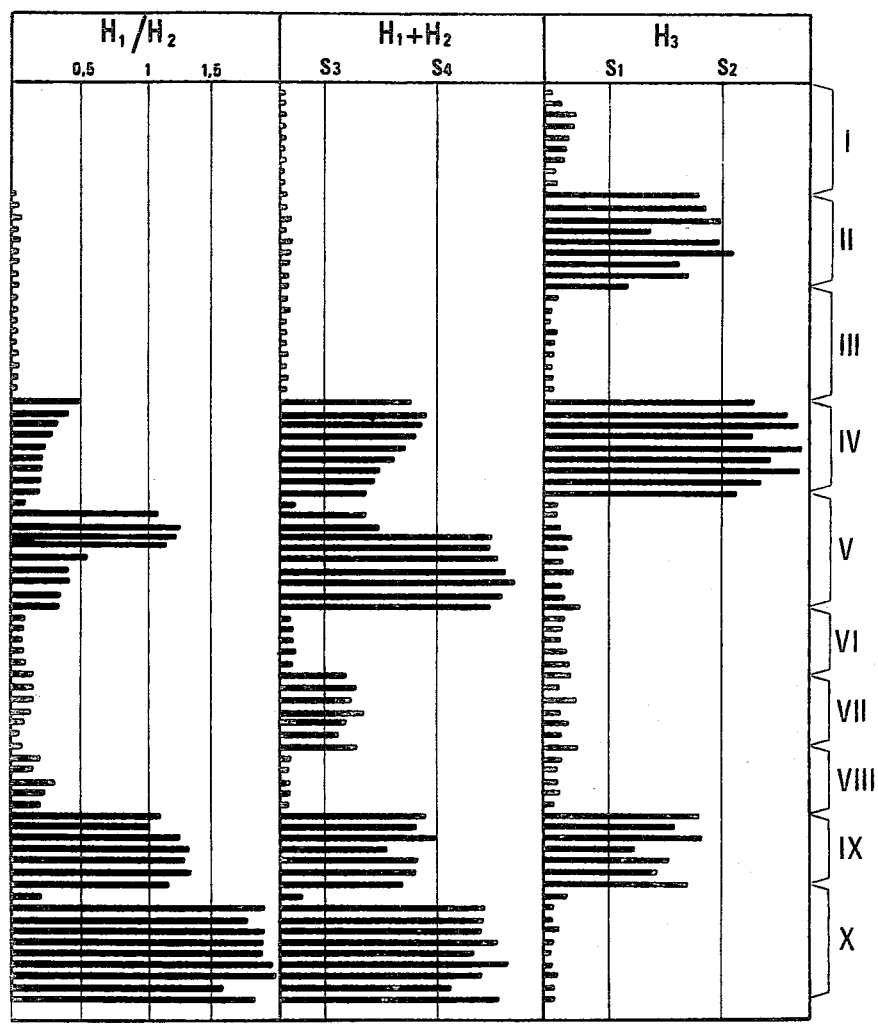
FIG. 3 illustrates a particular way of using and interpreting measurements effected on the drill cuttings, FIG. 4 diagrammatically illustrates the recording means.

FIG. 3 shows by way of example a particular embodiment of the method according to the invention, carried out during a drilling operation, the signal A being transmitted to the device 11, an embodiment of which is diagrammatically illustrated by FIG. 4.

The signal A delivered by the device 10 is transmitted simultaneously to three AND-gates or coincidence circuits 18 to 20 which also receive a validation signal from a clock or synchronization circuit 21. Each AND-gate 18 to 20 has its output terminal connected to the input terminal of a memory (memories 22 to 24 respectively) whose operation is synchronized by clock 21. The memories 22 and 23 are connected both to the input terminals of a dividing circuit 25 and to the input terminals of an adding circuit 26. The output terminals of the circuits 25, 26 and of memory 24 are connected to circuits 27 to 29 controlling plotting pens 30 to 32.

Between the instants $t_0$ and $t_1$, the clock circuit 21 validates the operation of AND-gate 18 and the value $H_1$ of signal A is recorded at 22. Between the instants $t_1$ and $t_2$, the clock 21 validates the operation of AND-gate 19 and the value $H_2$ of signal A is memorized at 23. Between the instants $t_2$ and $t_3$ the clock 21 validates the operation of AND-gate 20 and the value $H_3$ of signal A is introduced into memory 24.

At instant $t_3$, the clock 21 delivers a signal which resets to zero the memories 22 to 24.

The dividing circuit 25 then delivers a signal representative of the value $H_1/H_2$, which actuates the pen 30. Simultaneously the adding circuit 26 generates a signal representative of the value $[H_1+H_2,]$ this signal actuating the pen 31 while pen 32 is actuated by the signal delivered by memory 24. Then a new measuring cycle can occur. Measurements are carried out, as above indicated, on samples constituted by drill cuttings contained in the drill mud. For each analyzed sample the device 11 records on three distinct graphs the values of $H_1/H_2$, $H_1+H_2$, and $H_3$ versus the depth P from which the sample originates, this depth being determined by any known device 11a which will not be described in detail here and which co-operates with the apparatus illustrated by FIG. 1 to deliver a signal representative of the depth from which the sample originates.

There is thus provided on a recording chart which has been calibrated beforehand a three-track graph as illustrated in FIG. 3 and which makes it possible to accurately determine the oil-related characteristics of geological formations by considering the graphs showing the values of $(H_1+H_2)$ and $H_3$, the graph showing the values of the ratio $H_1/H_2$ indicating the nature (gas or oil) of the hydrocarbons contained in the geological formations of interest.

Thus, for example, the graph shows:

(a) the geological formations of no interest for hydrocarbon production (zones I, III, VI, VIII of the graph) for which the values of $H_3$ and $(H_1+H_2)$ are respectively lower than predetermined limit-values $S_1$ and $S_3$, (b) geological formations forming source rocks of average quality (zones II and IX) for which the values of $H_3$ are comprised between the limit values $S_1$ and $S_2$, (c) geological formations forming good source rocks—zone IV—(values of $H_3$ higher than the limit value $S_2$).

The level wherein lies a good source rock having thus been located, two cases can be found:

1. The source-rock is not buried at a sufficient depth (immature zone). In this case the value of $(H_1+H_2)$ remains low, in spite of a high value of $H_3$ (because no hydrocarbon have been generated)—zone II.

2. The source-rock is located in a zone where hydrocarbons have been generated. In such a case a high value of $H_3$ is associated to a high value of $H_1+H_2$—zone IV, (d) the geological formations corresponding to hydrocarbon containing reservoirs—zones V and X—for which the values of $H_3$ are low (generally lower than the limit $S_1$) and the values of $H_1+H_2$ are high (higher than the limit $S_4$).

Two case may then be found:

1. The reservoir contains mainly oil. Then the ratio $H_1/H_2$ is lower than 1—zone IV.

2. The reservoir contains mainly gas. Then the ratio $H_1/H_2$ is greater than 1—zone X.

(e) geological formations with only slight hydrocarbon shows—zone VII—for which the values of $(H_1+H_2)$ are comprised between the limit values $S_3$ and $S_4$.

The values $S_1$ and $S_4$ are selected by the operator, taking into account, for example, the economical criteria for the exploitation of hydrocarbon fields, etc . . .

For example, at the present time, reservoir zones for which the value of $S_4$ is greater than 4 kg hydrocarbons by ton of rock are found to be economically exploitable. All the so-collected data enable the field geologist to get a precise knowledge of the traversed geological formations.

These results may obviously by supplied by the data processing system 17 which may be, for example, a programmed computer and will not be described in detail.

The embodiment of apparatus of the invention, illustrated by FIG. 1, which is perfectly suitable for equipping a laboratory, may be too cumbersome when it is desired to build an equipment for use on the field.

It is then possible to turn to the embodiments illustrated by FIGS. 5 and 6.

In the embodiment illustrated by FIG. 5, only two heating means 4 and 6 are used to heat the lower and upper parts of tube 1.

To the heating means 4 is associated a programming means 33 which keeps the temperature in the lower part 5 of tube 1 at a value lower than 90° C. during the time interval $[t_0-t_1]$, then increases this temperature to a value comprised between 200° C. and 350° C. during the time interval $[t_1-t_2]$.

In this embodiment, heating means 6 maintains the upper part 7 of tube 1 at a temperature in the range from 550° to 600° C.

According to a modification (not shown) of this embodiment, heating means 4 keeps part 5 of tube 1 at a temperature in the range from 50° C. to 65° C.

To the heating means 6 is associated programming means which keeps the temperature of the upper part 7 of tube 1 in the range from 200° C. to 350° C. during the time interval $(t_0-t_2)$. At time $t_2$, this programming means produces a temperature increase of at least 20° C. per minute up to a value comprised between 550° C. and 600° C. At time $t_3$ the temperature is decreased to its initial value.

The embodiment illustrated by FIG. 6 uses only one heating means 6 to which is associated programming means 34. When the cup 12 is introduced in the tube 1, the temperature in the tube is increased to or maintained at a value in the range from 50° C. to 65° C. during time interval $(t_0-t_1)$. Then, the temperature is increased at a rate of at least 20° C. per minute to a value in the range from 200° C. to 350° C. during time interval $(t_1-t_2)$ and increased to a value in the range from 550° C. to 600° C. during time interval $(t_2-t_3)$. Then, the apparatus is cooled in a known manner before a new measuring cycle can start.

Such embodiments of apparatuses remain combersome either because of their heating means, or because of the cooling means required for lowering the temperature before analyzing a new sample.

Figure 7:
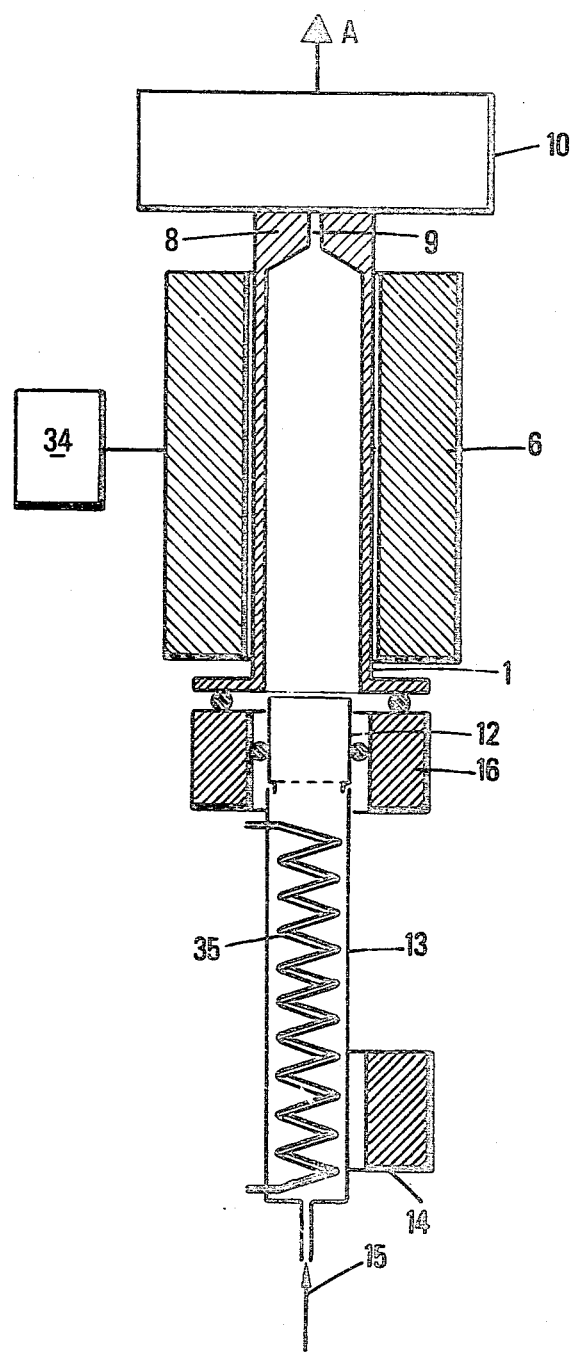

FIG. 7 shows the preferred embodiment of apparatus according to the invention which has proven to be the most compact and the most easily operated.

This embodiment differs from that illustrated by FIG. 6 in that there are provided within piston 14 means 35 for heating the carrier gas to a temperature in the range from 50° C. to 65° C. These means 35 consist, for example, of a heating electrical resistance. The programming means 34 is adapted to control the heating means 6 to maintain within tube 1 a temperature in the range from 200° C. to 350° C., then to raise this temperature to a value comprised between 550° C. and 600° C., as indicated hereinunder in the description of the operation of the device.

After the sample to be analyzed has been introduced into cup 12, piston 13 being in the position shown in FIG. 7, the carrier gas is introduced at time $t_0$ into the inner part of piston 13 and is heated to a temperature comprised in the range from 55° C. to 65° C. When flowing through the sample contained in the cup, the hot carrier gas drives along therewith the gaseous hydrocarbons which are initially present in this sample. At the same time the heating means 6 maintains within tube 1 a temperature in the range from 200° C. to 350° C. At instant t₁ the cup is introduced into tube 1. This causes vaporization of the liquid hydrocarbons initially present in the sample. At instant t₂, the programming means 34 raises the temperature within tube 1 at a rate of at least 20° C./minute to a value in the range from 550° C. to 600° C. at which the insoluble organic material of the sample is pyrolyzed. At instant t₃, piston 13 is retracted to its initial position, the flow of carrier gas is interrupted and the temperature within tube 1 is set back to a value in the range from 200° C. to 350° C.

What we claim is:

1. A method for rapidly evaluating at least one oil-related characteristic of a geological sediment using a small-sized sample thereof comprising determining the overall amount of hydrocarbons initially present in the sample and the overall amount of hydrocarbon products obtained by pyrolyzing the insoluble organic material contained in the sample, this method comprising the steps of
   (a) heating the sample to a first temperature suitable for releasing only the gaseous hydrocarbons initially contained in the sample,
   (b) determining a first parameter representative of the amount of these gaseous hydrocarbons,
   (c) heating the sample to a second temperature greater than said first temperature and suitable for vaporizing the whole amount of the liquid hydrocarbons initially contained in the sample, without pyrolyzing the insoluble organic material of the sample,
   (d) determining a second parameter representative of the amount of said liquid hydrocarbons,
   (e) heating the sample to a third temperature greater than said second temperature to pyrolyze the insoluble organic material contained in the sample,
   (f) determining a third parameter representing the amount of the hydrocarbon products resulting from this pyrolysis, and
   (g) deriving from said third parameter, together with said first and second parameters, the kind of hydrocarbons contained in the geological sediment and the degree of evolution of the insoluble organic material of the sample.

2. A method according to claim 1, wherein said second temperature is in the range from 200° C. to 350° C.

3. A method according to claim 1, wherein said third temperature is between 400° C. and 700° C.

4. A method according to claim 1, wherein, in heating the sample to said third temperature, the sample temperature increases at least 20° C./minute.

5. A method according to claim 1, wherein a carrier gas is passed through said sample to scavenge said sample.

6. A method according to claim 5, wherein said carrier gas is heated to said first temperature and heats said sample to said first temperature.

7. A method according to claim 1, wherein said first temperature is at most 90° C.

8. A method according to claim 7, wherein said second temperature is lower than 350° C.

9. A method according to claim 8, wherein said third temperature is between 400° C. and 700° C.

10. A method according to claim 7, wherein said first temperature is in the range from 50° C. to 65° C.

11. A method according to claim 10, wherein said second temperature is in the range of 200° C. to 350° C.

12. A method according to claim 11, wherein said third temperature is in the range of 550° C. to 600° C.

* * * * *